US011123457B2

(12) United States Patent
Highgate

(10) Patent No.: US 11,123,457 B2
(45) Date of Patent: Sep. 21, 2021

(54) NERVE CONTACT DEVICES

(71) Applicant: SUPERDIELECTRICS LTD, Royston (GB)

(72) Inventor: Donald James Highgate, Royston (GB)

(73) Assignee: SUPERDIELECTRICS LTD, Royston (GB)

(*) Notice: Subject to any disclaimer, the term of this patent is extended or adjusted under 35 U.S.C. 154(b) by 0 days.

(21) Appl. No.: 16/066,530

(22) PCT Filed: Dec. 21, 2016

(86) PCT No.: PCT/GB2016/054016
§ 371 (c)(1),
(2) Date: Jun. 27, 2018

(87) PCT Pub. No.: WO2017/115072
PCT Pub. Date: Jul. 6, 2017

(65) Prior Publication Data
US 2019/0015557 A1 Jan. 17, 2019

(30) Foreign Application Priority Data
Dec. 30, 2015 (GB) .................... 1523101

(51) Int. Cl.
H01M 4/60 (2006.01)
A61L 27/44 (2006.01)
(Continued)

(52) U.S. Cl.
CPC ............ A61L 27/446 (2013.01); A61L 27/48 (2013.01); A61L 27/50 (2013.01); H01M 4/602 (2013.01);
(Continued)

(58) Field of Classification Search
CPC ...... H01M 8/10; A61L 27/50; A61L 2430/14; A61L 2430/32; A61L 27/16; A61B 5/145; A61B 5/1468; A61B 5/14532; A61N 1/37512; A61N 1/36038; A61N 1/362; A61N 1/3605; A61N 1/36; A61N 1/375; C08F 2/48; C08F 226/10; C08F 220/44; C08F 220/40; C08F 2/44
(Continued)

(56) References Cited

U.S. PATENT DOCUMENTS

| 3,689,810 A * | 9/1972 | Walles ............... H01G 4/008 361/305 |
| 2008/0233454 A1* | 9/2008 | Capron ............... H01B 1/122 429/483 |
| 2019/0008999 A1* | 1/2019 | Highgate ............ A61L 27/16 |

FOREIGN PATENT DOCUMENTS

| EP | 2030668 | 3/2009 |
| GB | 2380055 | 3/2003 |

(Continued)

OTHER PUBLICATIONS

International Search Report/Written Opinion, PCT International Application No. PCT/GB2016/054016, dated Apr. 4, 2017.
(Continued)

Primary Examiner — Jon Eric C Morales
(74) Attorney, Agent, or Firm — Saliwanchik, Lloyd & Eisenschenk

(57) ABSTRACT

A material comprising an ionically conducting polymer (ICP) positioned between and in direct contact with two electronically conducting polymers (ECP).

14 Claims, 3 Drawing Sheets single junctions with catalyst inclusion

(51) Int. Cl.
    *A61L 27/50*     (2006.01)
    *H01M 8/1004*     (2016.01)
    *A61L 27/48*     (2006.01)
    *H01M 8/1067*     (2016.01)
    *H01M 8/1053*     (2016.01)

(52) U.S. Cl.
    CPC ....... *H01M 8/1004* (2013.01); *H01M 8/1053* (2013.01); *H01M 8/1067* (2013.01); *A61L 2430/32* (2013.01)

(58) Field of Classification Search
    USPC .................................. 429/483, 513; 427/115
    See application file for complete search history.

(56) References Cited

FOREIGN PATENT DOCUMENTS

| | | | | |
|---|---|---|---|---|
| GB | 2479449 | | 10/2011 | |
| GB | 2479449 A | * | 10/2011 | ............. A61L 27/26 |
| WO | 00/30201 | | 5/2000 | |

OTHER PUBLICATIONS

R. Ravichandran et al., "Applications of conducting polymers and their issues in biomedical engineering", Journal of the Royal Society, Jul. 7, 2010, vol. 7, No. Suppl 5, pp. S559-S579.
Matthew Anderson et al., "Peripheral Nerve Regeneration Strategies: Electrically Stimulating Polymer Based Verve Growth Conduits", Critical Reviews in Biomedical Engineering, Jan. 1, 2015, vol. 43, Nos. 2-3, pp. 131-159.

* cited by examiner

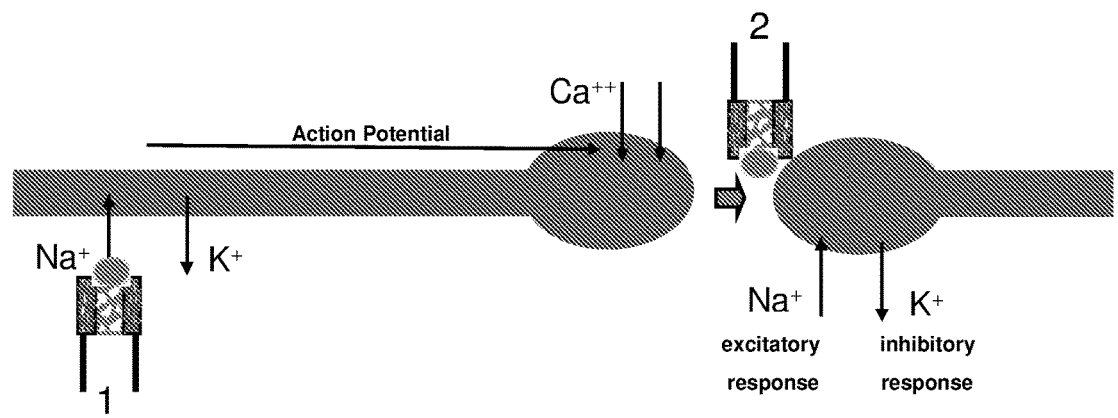
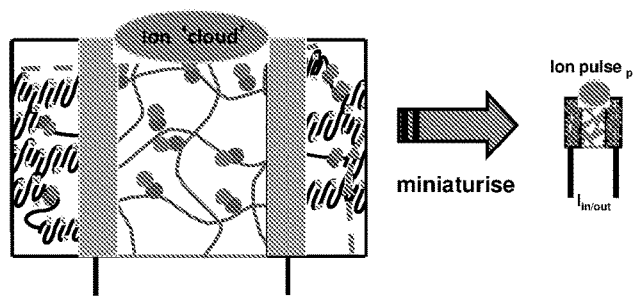
Apply input current ($I_{in}$)
⟹ generate ion pulse (p).
Feed in ion pulse
⟹ output electric current ($I_{out}$)
Figure 1: application of a bi-directional neural contact

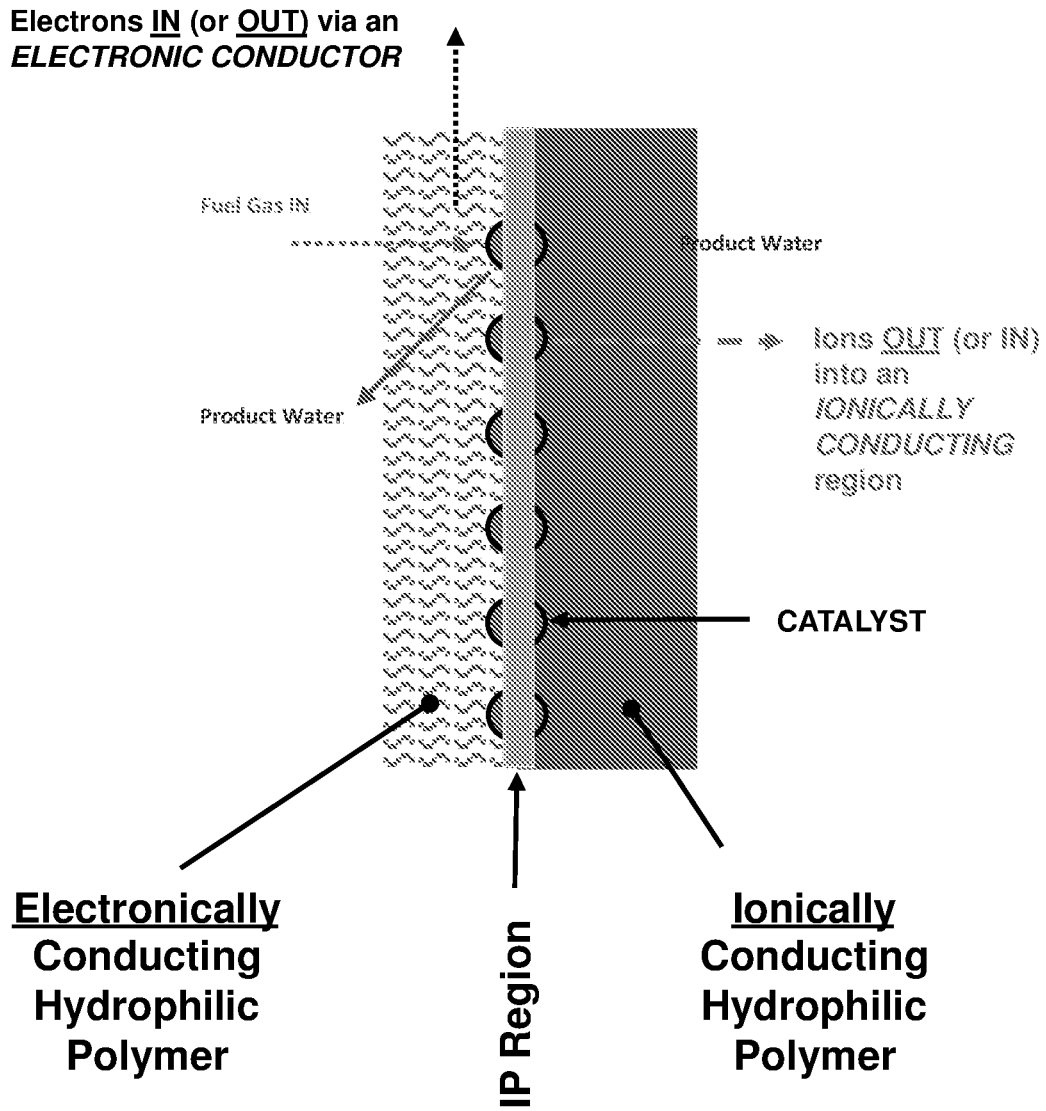
Figure 2: single junctions with catalyst inclusion

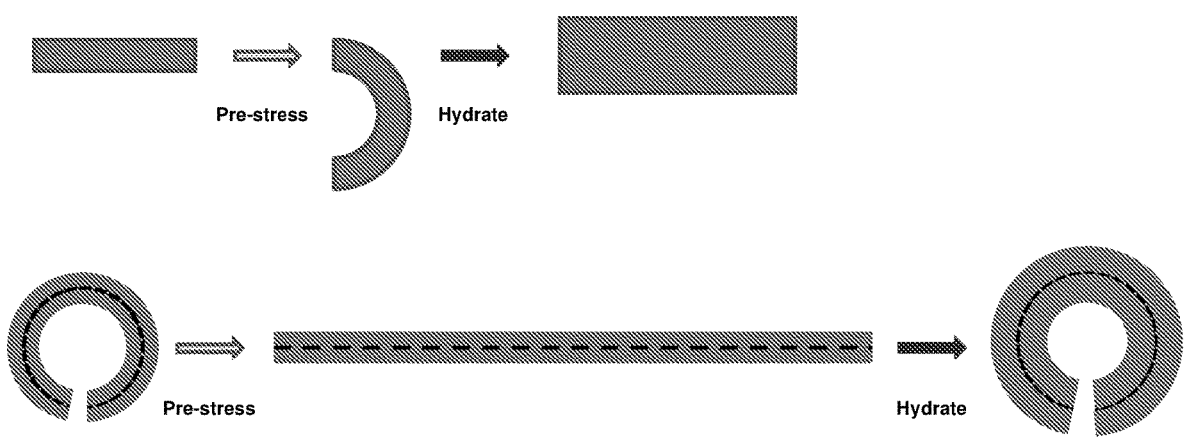
Figure 3: examples of hydrophilic pre-stressing and recovery

NERVE CONTACT DEVICES

CROSS-REFERENCE TO RELATED APPLICATIONS

This application is a national stage application of International Patent Application No. PCT/GB2016/054016, filed Dec. 21, 2016, which claims priority to Great Britain Application No. 1523101.2, filed Dec. 30, 2015, the disclosures of each of which are incorporated herein by reference in their entirety, including any figures, tables, and drawings.

FIELD OF THE INVENTION

This invention relates to polymer membranes and composite structures, and their use in nerve contact devices.

BACKGROUND OF THE INVENTION

Electrochemical devices that are required to interface between nervous tissue and electronic systems in prosthetic devices and applications involving functional electrical stimulation depend upon the transmission of and proper control of both ions and electrons.

Ionic conducting polymers (ICP) are materials in which the conduction process is principally dependent on ion transfer. Conventional solid ICP are typified by Nation®, a fluorocarbon-based cationic (proton) conductor which has become the industry standard material for the production of solid polymer fuel cells and electrolysers.

GB2380055A discloses hydrophilic ICP which allow the transmission of ions of various types, most importantly protons (specifically as hydronium ions in cationic ionomeric conductors (CE), but also including OH groups in alkaline-based ionic conductors (AE)). These ionically conducting materials have allowed the production of improved fuel cell and electrolyser MEAs in which both the ionic properties and the hydraulic properties of the ion-conducting membrane can be controlled.

Electronic conducting polymers (ECP) are well known, and are understood to mean materials in which the conduction process is principally dependent upon electron transfer. ECP include polyacetylene which has achieved electrical conductivities of $10^7$ S/m approximating to that of common metals, while commercial materials supplied as dispersions in water, e.g. polyethylenedioxythiophene:polystyrene suphonate (PEDOT:PSS, commercially available as Clevios 500; "Clevios" is a a registered Trade Mark), have a conductivity of $3\times10^4$ S/m and exceed the conductivity of graphite commonly used as a conductor in fuel cells. The biocompatibility of PEDOT:PSS has not been proven, but biocompatible electronic polymers do exist.

In a nerve contact device, it is necessary to transfer charge over the boundary between a metallic (electrode) and living tissue (for example, in order to control a prosthetic device). Because metallic conduction is based on electron flow, and neural tissue conduction on ion flow, a transition has to occur which requires an electrode interface.

Although both ionic and electronic propagation involves the movement of charged particles, the physics of each process is entirely different; e.g. metallic wires are excellent electronic conductors but are wholly ineffective as ionic transmission systems; likewise, liquid electrolytes are distinguished by excellent ionic transmission properties but very poor electronic conductivity.

GB2479449 provides a membrane material that can be produced by forming an interpenetrating network (IPN) between an ECP and a hydrophilic ICP. A membrane electrode assembly (MEA) can thus be produced in which all the principal components (except the catalyst) are replaced by polymeric materials. Importantly, such MEAs do not require external pressure to maintain contact between the components, and the invention permits the construction of lightweight MEAs and nerve contact devices. By using an IPN, a composite structure can be formed by means of which the ionic activity of viable nervous tissue can be transformed into an electronic signal for detection and use by electronic equipment including but not limited to the control of prosthetic devices.

SUMMARY OF THE INVENTION

Existing contact devices are principally unidirectional; they accept information from nerves but do not facilitate information input into nerves. Therefore, there is no feedback from a prosthetic device to a nerve, for example.

It has surprisingly been found that by linking an ECP on opposite sides of an ICP (such that a "sandwich" structure is formed), the resulting material can act as a nerve contact device that allows a bi-directional information flow. For example, in the case of a prosthetic limb, information can flow not only from the nerve tissue to the prosthetic limb, but from the prosthetic limb back to the nerve tissue. This may essentially enable sensory input from the prosthetic limb to the nerve tissue.

Therefore, according to a first aspect, the present invention is a material comprising an ionically conducting polymer (ICP) positioned between and in direct contact with two electronically conducting polymers (ECP).

Second, third and fourth aspects of the present invention are MEAs, nerve contact devices and prosthetic devices comprising the material as defined in the first aspect.

BRIEF DESCRIPTION OF DRAWINGS

FIG. 1 is a schematic view of application of a bi-directional neural contact, according to an embodiment of the subject invention.

FIG. 2 is a schematic view illustrating single junctions with catalyst inclusion, according to an embodiment of the subject invention.

FIG. 3 is a schematic view illustrating examples of hydrophilic pre-stressing and recovery, according to an embodiment of the subject invention.

DESCRIPTION OF THE INVENTION

While no material is exclusively restricted to one or the other mode of conduction, for practical purposes ratios of electronic:ionic conduction greater than 20:1 (for an ECP) and 1:20 (for an ICP) make it possible to construct working devices of acceptable efficiency.

As used herein, the term "material" should be understood to encompass composite materials, such as those used in accordance with the invention. Therefore, a "material" is preferably a "composite material".

As used herein, the term "monomer" takes its usual definition in the art, and so refers to a molecular compound that may chemically bind to other monomers to form a polymer.

As used herein, the term "hydrophilic polymer" refers to a polymer that dissolves in water when it is not cross-linked and absorbs water and swells to form a stable elastic solid when cross-linked.

A hydrophilic ICP may be produced by processes similar to those described in GB2380055A, e.g. by dissolving or mixing the monomers forming the ionically conductive material (e.g. AMPSA) in/with monomers chosen to provide hydrophilic properties (e.g. vinyl pyrrolidinone (VP) and/or 2-hydroxyethyl methacrylate (HEMA) and/or acrylonitrile (AN)) and polymerising and crosslinking the resulting monomer mixture by suitable means including gamma irradiation, UV irradiation in the presence of a suitable UV initiator and crosslinking agent or by thermal polymerisation.

Any ECP that is biocompatible is suitable for use in the invention. For example, an ECP could be formed from the polymerisation of electronically active amino acid(s) such as phenylalanine and/or tryptophan and/or histidine and/or tyrosine. Hydrophilic copolymers containing phenylalanine and tryptophan are most preferred. Likewise hydrophilic copolymers containing PEDOT:PSS may be suitable for use in the invention, but its biocompatibility is as yet unproven.

Metallic conductors, such as those that are necessary in a nerve contact device can be combined with an ECP to improve the overall efficiency of the MEA, e.g. in one example a thin interpenetrated layer of ECP is formed on the surface of the polymeric membrane (preferably a hydrophilic ionomeric membrane) and a metallic conductor in the form of discrete wires or a mesh is then laid onto the ECP, after which a second layer of ECP is deposited over the metallic conductor, making good electrical contact and offering a measure of corrosion protection for the metal components.

According to a first aspect, a material of the invention comprises an ionically conducting polymer (ICP) positioned between and in direct contact with two electronically conducting polymers (ECP).

In some embodiments, the direct contact is facilitated by the application of pressure.

In some embodiments, the ionically conducting polymer (ICP) is interlinked to each electronically conducting polymer (ECP) via an interpenetrated network.

When the junction between the polymeric components is an interpenetrated network, the resulting MEA operates substantially without the need for external pressure or support to maintain its structure and the electrical contacts between the components and layers thereof. This may be advantageous in circumstances where it is difficult to maintain pressure on the material/device.

The invention provides a method for the formation of interprenetrated networks between ionically conducting polymeric materials and electronically conducting polymers in which the junction comprises an interpenetrated region, by the polymerisation of one polymer from an initial monomer mixture in contact with the second material (either starting from the ECP or the ICP). Embodiments of the invention are lightweight, substantially non-metallic membrane electrode assemblies for use in, for example, nerve contact devices.

A material of the invention preferably has a conductivity of at least $5 \times 10^{-2}$ S/m $5 \times 10^{2}$ S/m. It can have a density of no more than 1.8 g/cc.

There are two routes to the production of electronic-ionic interfaces. The two routes arise because it is possible to take either a hydrophilic ionic material or an electronic material as the base structure (substrate). In the first instance, the electronic polymeric material is polymerised against the base material; in the second, it is the ionic material that is introduced as a monomer or pre-polymer and polymerised in situ against the substrate. Such products may appear to be identical although further analysis may show differences in performance.

GB2479449, which is incorporated herein by reference in its entirely, describes how electronically active polymers can be linked to ionically active polymers.

The present invention is based on the finding that bi-directional information flow is possible with the materials of the invention. In the case of a simple bi-layer of ECP and ICP, when it is placed near (or in contact with) a nerve, the material should experience sufficient ionic imbalance to allow a transient signal to be recorded by the electronics attached to the electronic component. The result is a small potential change compared with the surrounding (aqueous) structure which will slowly return to 'neutral' as the ion signal decays.

Without wishing to be bound by theory, the tri-layer material of the invention allows for any charge imbalance to be dissipated rapidly (so that repeated signal pulse can be applied). This enables an electronic signal to be received and transmitted to nerve tissue.

The species of ion that is generated in the material of the invention (ICP) depends upon the material of the junction and upon the aqueous solution used to hydrate one or more of the polymeric components. For example, if the system is hydrated in NaCl solution, then the predominant charge carriers within the ionic conductor are sodium ions; if KCl is the hydrating solution, then $K^+$ ions will result.

It is possible and in some circumstances advantageous to incorporate catalyst materials at or within one or both of the interfaces.

FIG. 1 is a schematic illustrating the invention.

In some embodiments, a material of the invention comprises a catalyst (typically Pt or similar as powder, fibres or thin micro-porous film). This may significantly increase the electro-chemical options for the operation of the device. In particular, it can reduce the potential necessary to initiate operation of the device as a generator of ions or electrons. This is illustrated in FIG. 2 (single junction/interface shown). The critical contact region is formed by the interpenetrating (IP) region between the two polymers (i.e. between the electronically conducting hydrophilic polymer and the ionically conducting hydrophilic polymer). It is (i) permanent, (ii) flexible, and (iii) gas, water, and solute permeable.

In a preferred embodiment, the material has been pre-stressed. Preferably, the material that has been pre-stressed is hydrophilic and/or cross-linked. Preferably, the pre-stressed material can be returned to its original shape by hydrating the material in water. Such structures can return to their original shape when hydrated in water or suitable aqueous solutions. The resulting structure will be larger (in at least one dimension) because of the uptake of water during the hydration process. Although shape change (recovery) may be initiated by heating, hydration activated shape recovery is particularly appropriate to biological systems because it will proceed at normal body temperature.

Many shapes and recovery procedures can be used; however, one particular form is of particular value as a nerve contact device. In this case, the junction region is made as a tight spiral; then pre-stressed in (for example) a straight strip; on hydration it 'curls up' and re-assumes the spiral form. In this example the device can be made to fold round the nerve fibre as illustrated in FIG. 3.

The invention claimed is:

1. A material comprising a tri-layer polymeric system, wherein the tri-layer polymeric system consists of an ionically conducting polymer (ICP) positioned between and in direct contact with two electronically conducting polymers (ECP), wherein the ICP is hydrophilic.

2. The material according to claim 1, wherein the direct contact is facilitated by the application of pressure.

3. The material according to claim 1, obtainable by polymerisation of monomers to form the ICP in contact with each ECP.

4. The material according to claim 1, obtainable by polymerisation of monomers to form each ECP in contact with the ICP.

5. The material according to claim 1, wherein the ICP is interlinked to each ECP via an interpenetrated network.

6. The material according to claim 4, wherein the polymerisation is conducted in defined areas only.

7. The material according to claim 1, which has a conductivity of at least $5 \times 10^{-2}$ S/m.

8. The material according to claim 1, wherein the ICP is cross-linked.

9. The material according to claim 1, which is a spiral shape.

10. The material according to claim 1, which has been pre-stressed.

11. The material according to claim 10, which is a spiral shape, and which has been pre-stressed into a substantially straight strip, such that it can fold around a nerve fibre.

12. A membrane-electrode assembly comprising, as the membrane, the material according to claim 1.

13. A nerve contact device comprising the material according to claim 1.

14. A prosthetic device comprising, at a surface intended to contact viable nerves, the material according to claim 1.

* * * * *